US008909323B2

(12) United States Patent
Baumgart (10) Patent No.: US 8,909,323 B2
(45) Date of Patent: Dec. 9, 2014

(54) SYSTEM FOR PROCESSING ANGIOGRAPHY AND ULTRASOUND IMAGE DATA (75) Inventor: John Baumgart, Hoffman Estates, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 806 days.

(21) Appl. No.: 12/836,602

(22) Filed: Jul. 15, 2010

(65) Prior Publication Data

US 2011/0034801 A1 Feb. 10, 2011

Related U.S. Application Data (60) Provisional application No. 61/231,717, filed on Aug. 6, 2009.

(51) Int. Cl.
| | | |
|---|---|---|
| *A61B 8/14* | (2006.01) | |
| *A61B 6/00* | (2006.01) | |
| *A61B 8/12* | (2006.01) | |
| *A61B 8/00* | (2006.01) | |
| *A61B 8/08* | (2006.01) | |
| *A61B 5/00* | (2006.01) | |

(52) U.S. Cl.
CPC ............... *A61B 6/504* (2013.01); *A61B 6/4441* (2013.01); *A61B 6/463* (2013.01); *A61B 6/5247* (2013.01); *A61B 8/12* (2013.01); *A61B 8/4416* (2013.01); *A61B 8/463* (2013.01); *A61B 8/5238* (2013.01); *A61B 5/489* (2013.01)
USPC ............ 600/427; 600/437; 600/443; 600/467

(58) Field of Classification Search
None
See application file for complete search history.

(56) References Cited

U.S. PATENT DOCUMENTS

| | | | | |
|---|---|---|---|---|
| 4,987,412 | A | * | 1/1991 | Vaitekunas et al. ........... 345/635 |
| 5,672,877 | A | | 9/1997 | Liebig et al. |
| 6,148,095 | A | * | 11/2000 | Prause et al. .................. 382/131 |
| 6,631,284 | B2 | | 10/2003 | Nutt et al. |
| 7,292,715 | B2 | * | 11/2007 | Furnish .......................... 382/128 |
| 7,583,857 | B2 | | 9/2009 | Xu et al. |
| 7,603,165 | B2 | | 10/2009 | Townsend et al. |
| 2005/0031176 | A1 | * | 2/2005 | Hertel et al. .................. 382/128 |
| 2006/0036167 | A1 | * | 2/2006 | Shina ............................ 600/433 |
| 2006/0041180 | A1 | * | 2/2006 | Viswanathan et al. .......... 600/11 |
| 2006/0072808 | A1 | | 4/2006 | Grimm et al. |
| 2006/0241465 | A1 | * | 10/2006 | Huennekens et al. ........ 600/458 |
| 2007/0016029 | A1 | * | 1/2007 | Donaldson et al. ........... 600/437 |

(Continued)

*Primary Examiner* — Long V Le
*Assistant Examiner* — Bradley Impink
(74) *Attorney, Agent, or Firm* — Brennan K Bradley (57) ABSTRACT

A system provides a single composite image including multiple medical images of a portion of patient anatomy acquired using corresponding multiple different types of imaging device. A display processor generates data representing a single composite display image including, a first image area showing a first image of a portion of patient anatomy acquired using a first type of imaging device, a second image area showing a second image of the portion of patient anatomy acquired using a second type of imaging device different to the first type. The first and second image areas include first and second markers respectively. The first and second markers identify an estimated location of the same corresponding anatomical position in the portion of patient anatomy in the first and second images respectively. A user interface enables a user to move at least one of, (a) the first marker in the first image and (b) the second marker in the second image, to correct the estimated location so the first and second markers identify the same corresponding anatomical position in the portion of patient anatomy.

13 Claims, 6 Drawing Sheets

(56) References Cited

U.S. PATENT DOCUMENTS

| | | |
|---|---|---|
| 2007/0038061 A1* | 2/2007 | Huennekens et al. ........ 600/407 |
| 2007/0043292 A1* | 2/2007 | Camus et al. ................ 600/443 |
| 2007/0165141 A1* | 7/2007 | Srinivas et al. .............. 348/571 |
| 2008/0095465 A1 | 4/2008 | Mullick et al. |
| 2008/0247622 A1 | 10/2008 | Aylward et al. |
| 2008/0269599 A1 | 10/2008 | Csavoy et al. |
| 2009/0196470 A1 | 8/2009 | Carl et al. |
| 2010/0063400 A1* | 3/2010 | Hall et al. .................... 600/466 |

\* cited by examiner

SYSTEM FOR PROCESSING ANGIOGRAPHY AND ULTRASOUND IMAGE DATA

This is a non-provisional application of provisional application Ser. No. 61/231,717 filed 6 Aug. 2009, by J. Baumgart.

FIELD OF THE INVENTION

This invention concerns a system for providing a single composite image including multiple medical images of a portion of patient anatomy acquired using corresponding multiple different types of imaging device.

BACKGROUND OF THE INVENTION

Angiography imaging modality and intravascular ultrasound (IVUS) imaging modality devices are both used to assess condition of patient blood vessels and each type of device has respective features and advantages. Known systems that use both these types of imaging modality device concurrently require that a location of an IVUS transducer be detected in live angiography images acquired during retraction (pullback) of an IVUS device from a vessel, for example. An intravascular ultrasound (IVUS) medical imaging modality device uses a catheter with a miniaturized ultrasound probe attached to a distal end of the catheter. The proximal end of the catheter is attached to computerized ultrasound equipment. An IVUS device acquires an image inside a blood vessel through a surrounding blood column and the images show the endothelium (inner wall) of the blood vessel in living individuals. An acquired image is mapped to an angiographic X-ray image that was acquired in the presence of contrast agent to allow visualization of vasculature. In order to visualize an artery or vein, an angiographic method is used involving positioning a soft and pliable tip of a guidewire, usually 0.36 mm (0.014") diameter and about 200 cm long. The guidewire is steered from outside the body, through angiography catheters and guided into a blood vessel branch to be imaged. The ultrasound catheter tip is slid in over the guidewire and positioned, using angiography techniques so that the tip is at the farthest away position to be imaged. Sound waves emitted from the catheter tip are usually in the 10-20 MHz range, and the catheter receives and conducts return echo information to external computerized ultrasound equipment. The equipment constructs and displays real time ultrasound images of a thin section of the blood vessel currently surrounding the catheter tip at a typical 30 frames per second rate. The guide wire is kept stationary and the ultrasound catheter tip is slid backwards, usually under motorized control at a pullback speed of 0.5 min/s, for example.

The detected trajectory of the ultrasound catheter tip as it is slid backwards is prone to error which shows as anatomic mismatch and mis-alignment between an angiographic X-ray image and an IVUS imaging dataset. This is because there may be significant motion during pullback of the ultrasound catheter tip (e.g., cardiac or breathing motion) and there is also no contrast agent present during pullback leading to an absence of landmarks in the X-ray image that would support location of an ultrasound transducer in a vessel. A system according to invention principles addresses these deficiencies and related problems.

SUMMARY OF THE INVENTION

A system corrects mis-alignment between a detected trajectory of an interventional ultrasound (IVUS) transducer during an IVUS retraction (pullback) procedure in which IVUS data is used in conjunction with angiographic X-ray data. A system provides a single composite image including multiple medical images of a portion of patient anatomy acquired using corresponding multiple different types of imaging device. A display processor generates data representing a single composite display image including, a first image area showing a first image of a portion of patient anatomy acquired using a first type of imaging device, a second image area showing a second image of the portion of patient anatomy acquired using a second type of imaging device different to the first type. The first and second image areas include first and second markers respectively. The first and second markers identify an estimated location of the same corresponding anatomical position in the portion of patient anatomy in the first and second images respectively. A user interface enables a user to move at least one of, (a) the first marker in the first image and (b) the second marker in the second image, to correct the estimated location so the first and second markers identify the same corresponding anatomical position in the portion of patient anatomy.

DETAILED DESCRIPTION OF THE INVENTION

Figure 1:
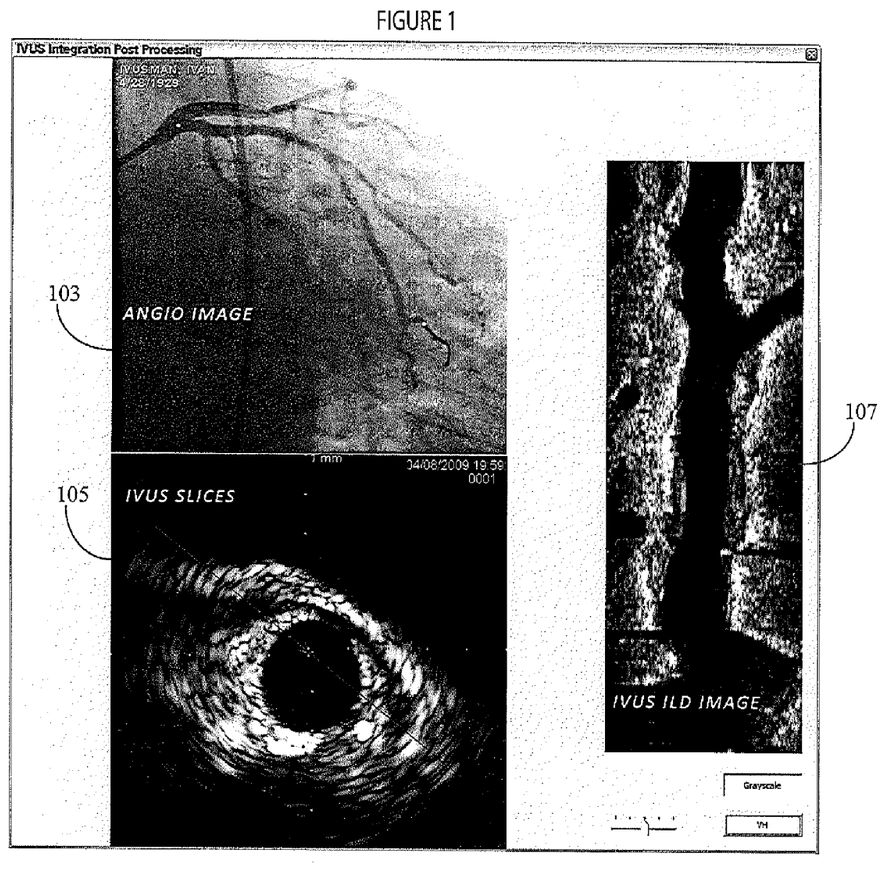
FIG. 1 illustrates a composite image showing co-registered angiography and IVUS image data.

A system corrects mis-alignment (mis-registration) between a detected trajectory of an intravascular ultrasound (IVUS) transducer during an IVUS pullback procedure in which IVUS image data is used and aligned with angiographic X-ray data using timestamps and device localization to permit patient diagnosis. The system enables a user to correct a mis-registration between co-registered angiography and IVUS images. FIG. 1 illustrates a composite image showing angiography image 103 co-registered with IVUS image slice 105 presented together with an IVUS ILD (in-line display) pullback image 107 derived by retracting an IVUS catheter from a vessel. A user corrects mis-registration between co-registered angiography and IVUS images by selecting a point on either displayed image and moving it to a point that represents a correct registration with a marker present on the other image. A user may choose to correct either on the angiography image or on an IVUS image and the correction may be applied in different ways.

Figure 2:
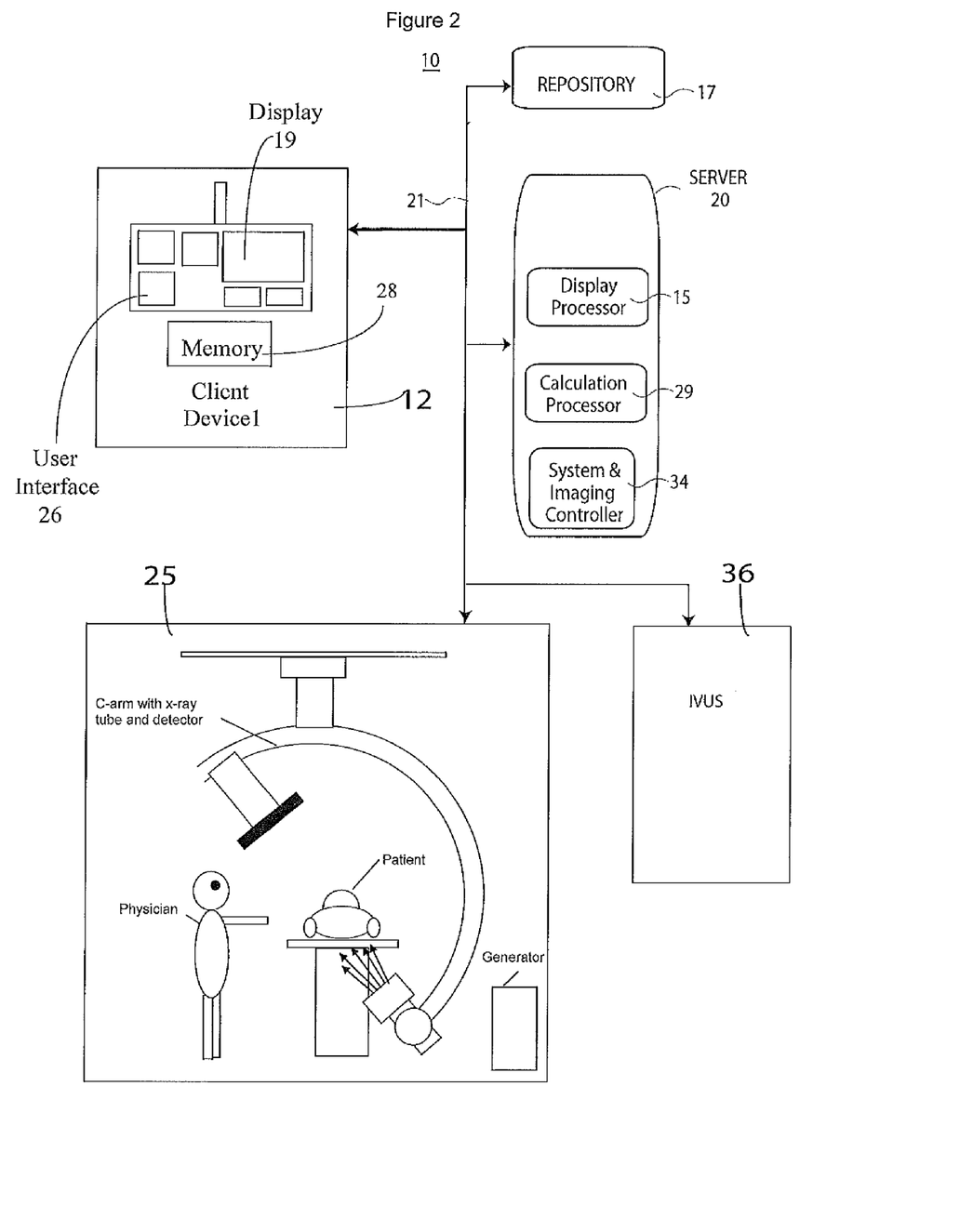
FIG. 2 shows a system for providing a single composite image including multiple medical images of a portion of patient anatomy acquired using corresponding multiple different types of imaging device, according to invention principles.

FIG. 2 shows system 10 for providing a single composite image including multiple medical images of a portion of patient anatomy acquired using corresponding multiple different types of imaging device. System 10 includes one or more processing devices (e.g., workstations or portable devices such as notebooks, Personal Digital Assistants, phones) 12 that individually include a user interface control device 26 such as a keyboard, mouse, touchscreen, voice data entry and interpretation device and memory 28. System 10 also includes at least one repository 17, X-ray imaging modality system 25 and intravascular ultrasound (IVUS) medical imaging modality device 36 and server 20 intercommunicating via network 21. In an alternative embodiment imaging modality devices 25 and 36 may either comprise MR (magnetic resonance), CT scan or PET scan devices, for example). X-ray modality system 25 comprises a C-arm X-ray radiation source and detector device rotating about a patient table and an associated electrical generator for providing electrical power for the X-ray radiation system. The display images are generated in response to predetermined user (e.g., physician) specific preferences. At least one repository 17 stores medical image studies for multiple patients in DICOM compatible (or other) data format. A medical image study individually includes multiple image series of a patient anatomical portion which in turn individually include multiple images. Server 20 includes display processor 15, calculation processor 29 and system and imaging controller 34. Display processor 15 provides data representing display images comprising composite angiography and IVUS images and a Graphical User Interface (GUI) for presentation on display 19 of processing device 12. Imaging controller 34 controls operation of imaging device 25 in response to user commands entered via user interface 26. In alternative arrangements, one or more of the units in server 20 may be located in device 12 or in another device connected to network 21.

At least one repository 17 stores a first and second sequential series of images concurrently acquired at time stamped acquisition times using X-ray imaging device 25 and intravascular ultrasound imaging device 36 respectively. Display processor 15 generates data representing a single composite display image including, a first image area showing a first image of a patient vessel structure acquired using first type of imaging device 25, a second image area showing a second image of the patient vessel structure acquired using second type of imaging device 36 different to the first type. The first and second image areas include first and second markers respectively. The first and second markers identify a first estimated location of the same corresponding anatomical position in the patient vessel structure in the first and second images respectively. User interface 26 enables a user to move at least one of, (a) the first marker in the first image and (b) the second marker in the second image, to correct the first estimated location so the first and second markers identify the same corresponding anatomical position in the patient vessel structure. Calculation processor 29 adjusts a timestamp of the time stamped acquisition times in response to correction of the first estimated location.

Figure 4:
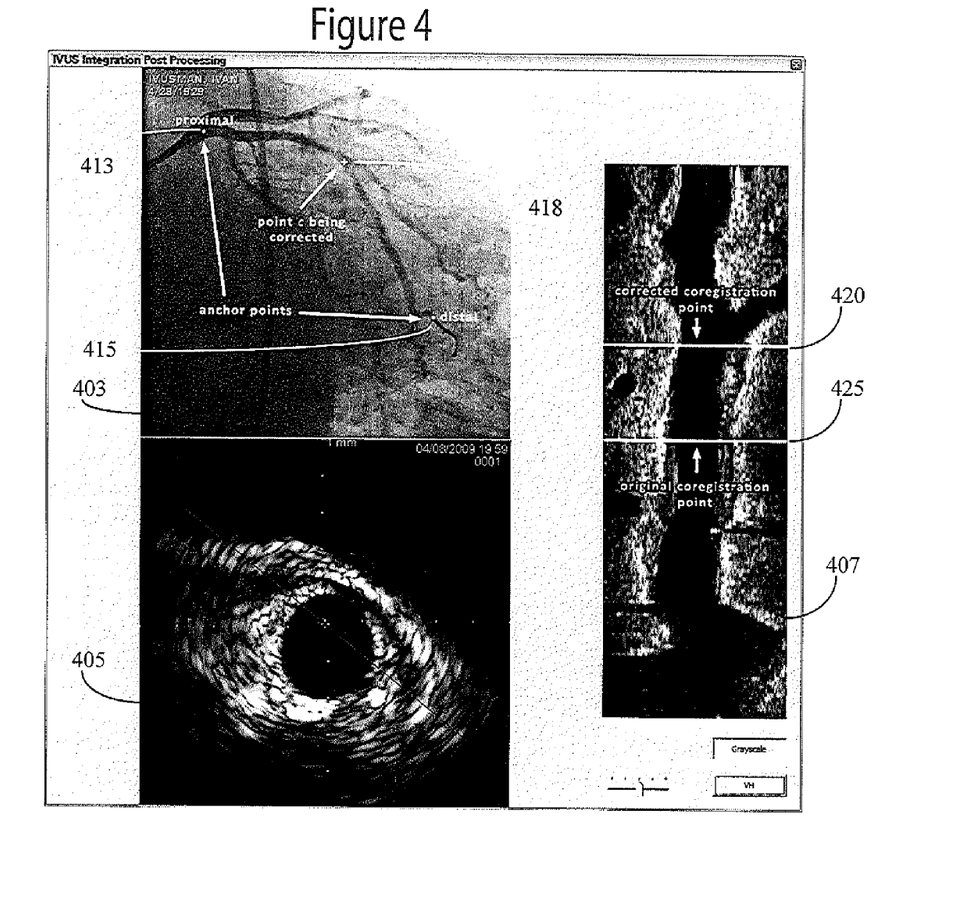
FIG. 4 illustrates correction of a time associated with a point in an angiography image, according to invention principles.

FIG. 4 illustrates correction of a time associated with a point in an angiography image. A user may indicate that a different location in an IVUS image derived by retraction of a catheter corresponds to a specific point (i.e. is co-registered with the specific point) on an angiography image. In response to this indication, timestamps associated with the co-registered points on the angiography image are automatically changed according to the following rules. A first correction offsets points equally according to a correction specified by a user also a first point that is corrected becomes an anchor point. Anchor points are not changed in response to new corrections and in response to a correction being applied between two anchor points, the correction applied to the remaining points between the anchor points is determined by interpolation. If a correction is applied that is not between anchor points, but at least one anchor point already exists, a correction applied to remaining points between the anchor point and the correction point is interpolated. A correction applied to remaining points from the correction point and the start or end of the map is interpolated between the anchor point and the time associated with the end of IVUS catheter pullback in the opposite direction of the anchor point.

Let t be the original time of the point being corrected and t' be the corrected time, $t_p$ and $t_d$ are the times of the proximal and distal anchor points. For points i between the proximal and distal anchor points ($i_p$ and $i_d$) that bound the point $i_c$ being corrected, the new time is defined as:

$$t'_i = \begin{cases} t_i + \dfrac{(t'-t)(t_i - t_p)}{t - t_p}, & (i_c < i < i_p \text{ and } i_p \text{ is defined) or } (i_d \text{ is undefined}) \\ t_i + \dfrac{(t'-t)(t_i - t_d)}{t - t_d}, & (i_d < i < i_c \text{ and } i_d \text{ is defined) or } (i_p \text{ is undefined}) \end{cases}$$

In FIG. 4, a user adjusts a time of point C 418 between proximal and distal anchor points 413 and 415 respectively, shown on angiography image 403 by selecting a different row (row 420 instead of row 425) within the IVUS ILD image 407, where each row corresponds to a known acquisition time. Alternatively a user may select a new slice 405 in the IVUS dataset used to build the ILD image. The time at point C 418 is adjusted to match the corrected time. Further, remaining points are automatically adjusted for co-registration using the interpolation rules.

In FIG. 4, a timestamp associated with distal point 415 on angiography X-ray image 403 is 0.0 seconds, a timestamp associated with proximal point 413 is 120.0 seconds, and the timestamp (t) on point C 418, corresponding to an original co-registration point on the IVUS ILD image, is 60.0 seconds, and both the proximal and distal points are anchor points. A user interacts with ILD image 407 to correct the timestamp of point C 418 to 40.0 seconds to provide a corrected co-registration point. The value (t'−t)=−20.0 sec. The remaining points of the pullback image 407 are also adjusted according to the equations above. For a point between C 418 and distal point 415 having an initial timestamp of 25.0 sec, the new timestamp is:

$$t'_i = 25 + \frac{-20(25-0)}{60-0} = 16.667 \text{ sec.}$$

Likewise, for a point between C 418 and proximal point 413 having an initial timestamp of 90.0 sec, the new timestamp is:

$$t'_i = 90 + \frac{-20(90-120)}{60-120} = 80 \text{ sec.}$$

Alternatively, a user may specify that a different location in angiography image 403 corresponds to a selected time (represented by IVUS slice 405 and/or ILD marker) in the IVUS dataset. In this case, co-registration positions are moved along the previously tracked vessel centerline according to the same rules used with anchor points. The index of the points comprising the tracked vessel centerline is used to determine the new position, and a new index to use is determined by interpolation in a similar manner to the correction of timestamps. Specifically, let $i_a$ be an index of a vessel centerline (v) point closest to a point being corrected, $i'_a$ be the index of the vessel centerline point it is being corrected to, and $i_p$ and $i_d$ are the indices of points on the vessel centerline corresponding to proximal and distal anchor points. For points $k_{p+1}$ through $k_{d-1}$, the correction of the index $i_k$ is:

$$\Delta i_k = \begin{cases} \dfrac{(i'_a - i_a)(i_k - i_p)}{i_a - i_p}, & (i_a < i < i_p \text{ and } i_p \text{ is defined}) \text{ or } (i_d \text{ is undefined}) \\ \dfrac{(i'_a - i_a)(i_d - i_k)}{i_a - i_d}, & (i_d < i < i_a \text{ and } i_d \text{ is defined}) \text{ or } (i_p \text{ is undefined}) \end{cases}$$

The new location that is to be used to correct point $a_k$, where a represents the points on the tracked centerline, is:

$$a'_k = v_{i_k + \Delta i_k}$$

Figure 5:
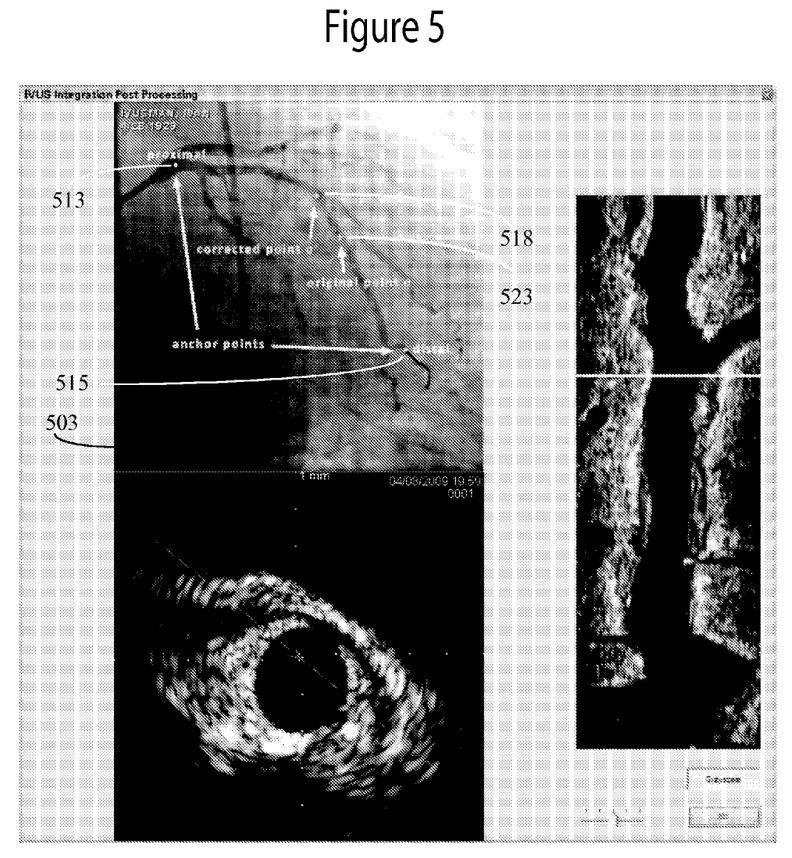
FIG. 5 illustrates correction of the position of a point on an angiography image, according to invention principles.

FIG. 5 illustrates correction of the position of point a 523 to point 518 on angiography image 503. In FIG. 5, a user adjusts the position of point a at a specific time by moving the location along the known vessel centerline to match the anatomy shown in the IVUS dataset. The location of the point a is updated to reflect the new location. Locations of other points are adjusted according to the interpolation rules above.

In FIG. 5, proximal anchor point 513 is located at (210, 110), distal anchor point 515 is located at (525,360), point a is located at (430,200), and the corrected point a' is located at (400,150). A map of the vessel contains 500 points equally spaced along the map and has distal point 515 as point 0, proximal point 513 as point 499, the original point a closest to point 200, and the corrected point a' closest to point 280. The change in the index for point a ($i'_a - i_a$) is (280-200), or 80. The remaining points in the co-registration have their positions changed according to the equation above. For a point between a and distal point 515 that is closest to index 100, the index used to determine its new location is:

$$i'_k = 100 + \frac{80(100 - 0)}{200 - 0} = 140$$

The new location of the point is 140 in the 500 point map of the vessel centerline. Likewise, for a point between a and proximal anchor point 513 that is closest to point 350 of the centerline, the index used to determine its new location is:

$$i'_k = 350 + \frac{80(350 - 499)}{200 - 499} = 390$$

Figure 3:
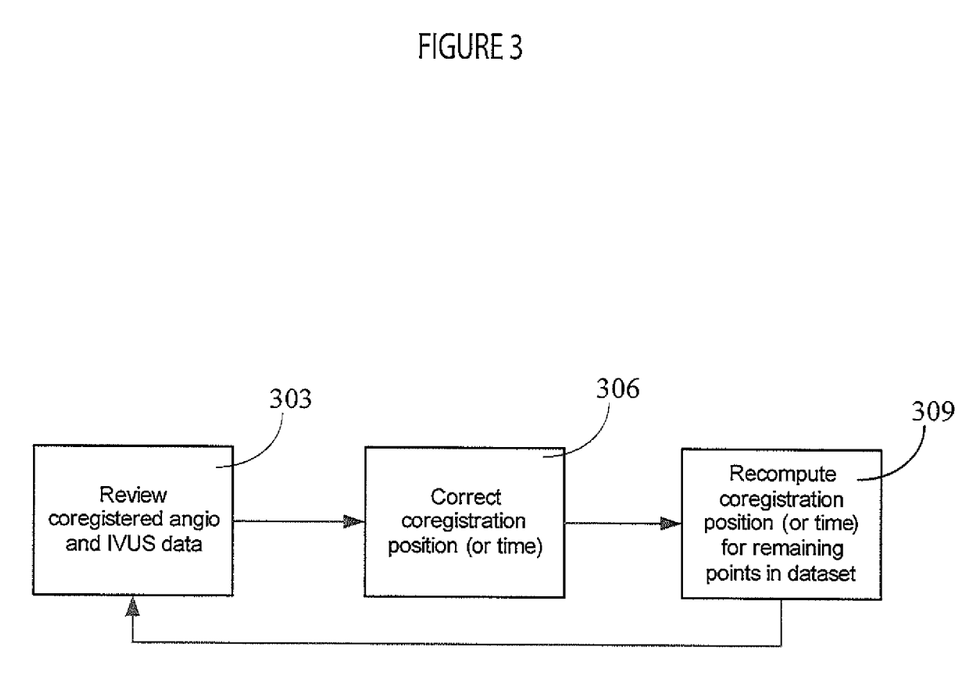
FIG. 3 shows a flowchart of a process for aligning multiple medical images of a portion of patient anatomy acquired using corresponding multiple different types of imaging device, according to invention principles.

FIG. 3 shows a flowchart of a process for aligning multiple medical images of a portion of patient anatomy acquired using corresponding multiple different types of imaging device. System 10 (FIG. 2) in step 306 automatically corrects a registration position (or time) of a point in an angiographic image relative to a corresponding position in an IVUS image in response to a user identifying a corrected time or position of the point in one image type relative to the other image type in step 303. System 10 (FIG. 2) in step 309 using interpolation, automatically corrects registration positions (or times) of remaining points in the angiographic image relative to the IVUS image. The process of FIG. 3 is iteratively repeated as needed.

Figure 6:
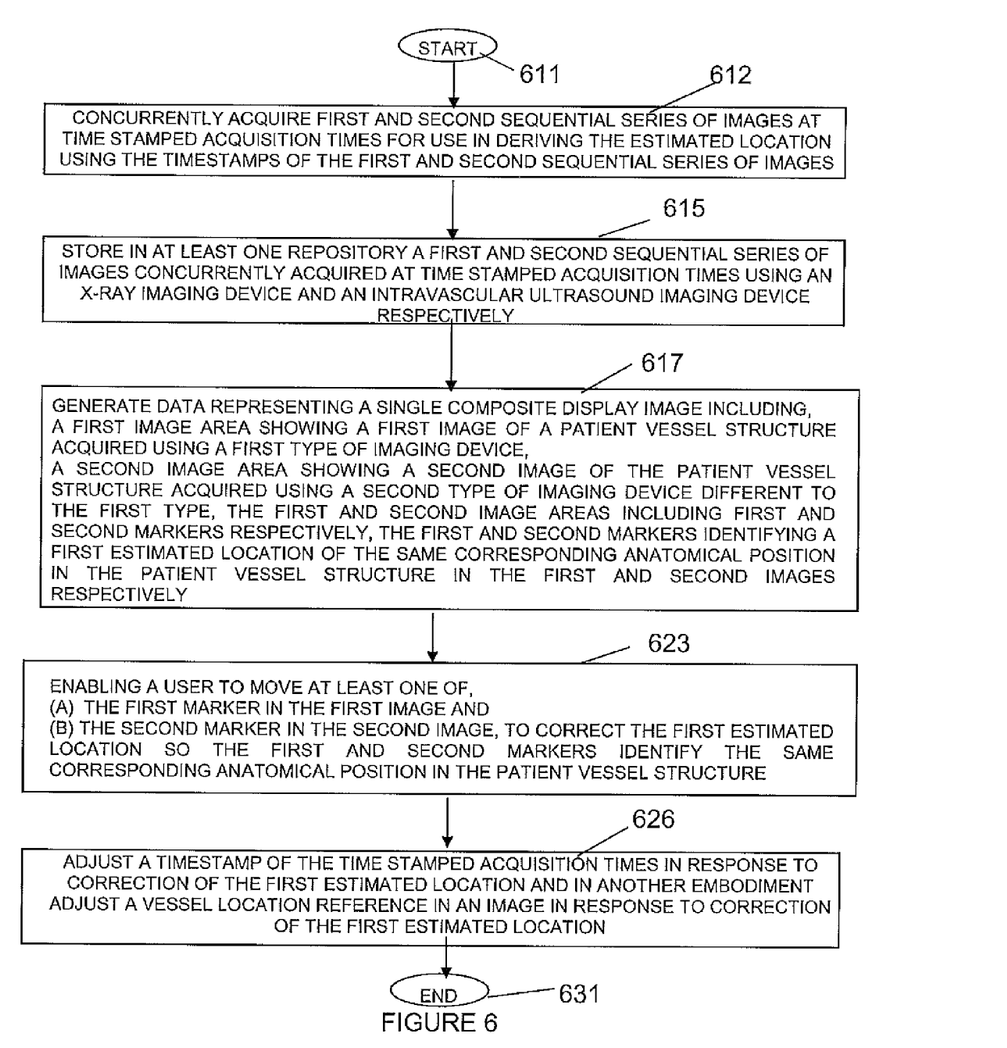
FIG. 6 shows a flowchart of a process used by a system for providing a single composite image including multiple medical images of a portion of patient anatomy acquired using corresponding multiple different types of imaging device, according to invention principles.

FIG. 6 shows a flowchart of a process used by system 10 (FIG. 2) for providing a single composite image including multiple medical images of a portion of patient anatomy acquired using corresponding multiple different types of imaging device. In step 612 following the start at step 611, first and second different types of imaging device comprising X-ray imaging device 25 and intravascular ultrasound imaging device 36 concurrently, respectively acquire first and second sequential series of images at time stamped acquisition times. The first and second types of imaging device may comprise at least two of, (a) an X-ray imaging device, (b) an ultrasound imaging device, (c) an MR imaging device, (d) a CT scan imaging device and (e) a nuclear imaging PET scanner device.

In step 615 system 10 stores in at least one repository 17 the first and second sequential series of images concurrently acquired at time stamped acquisition times. Display processor 15 in step 617 generates data representing a single composite display image including, a first image area showing a first image of a patient vessel structure acquired using a first type of imaging device (X-ray device 25), a second image area showing a second image of the patient vessel structure acquired using a second type of imaging device (IVUS device 36) different to the first type. The first and second image areas include first and second markers respectively. The first and second markers identify a first estimated location of the same corresponding anatomical position in the patient vessel structure in the first and second images respectively. The estimated location is derived using the timestamps of the first and second sequential series of images. The first and second markers represent one of, (a) a proximal point and (b) a distal point of the vessel structure.

In one embodiment, the first and second image areas include third and fourth markers respectively. The third and fourth markers identify a second estimated location of the same corresponding anatomical position in the patient vessel structure in the first and second images respectively. Further, user interface 26 enables a user to move at least one of, (a) the third marker in the first image and (b) the fourth marker in the second image, to correct the second estimated location so the third and fourth markers identify the same corresponding anatomical position in the patient vessel structure. The first and second markers represent a proximal point of the vessel structure and the third and fourth markers represent a distal point of the vessel structure.

In step 623 user interface 26 enables a user to move at least one of, (a) the first marker in the first image and (b) the second marker in the second image, to correct the first estimated location so the first and second markers identify the same corresponding anatomical position in the patient vessel structure. Calculation processor 29 adjusts a vessel location reference associated with a timestamp of the time stamped acquisition times in response to correction of the first estimated location. The vessel location reference is associated with a location on a line through a vessel in the vessel structure. In step 626 calculation processor 29 adjusts a timestamp of the time stamped acquisition times in response to correction of the first estimated location by (e.g., linearly) interpolating timestamp adjustments between the corrected first estimated location and a second point in the vessel structure. In another embodiment processor 29 adjusts a vessel location reference in an image and the vessel location reference is associated with a timestamp of the time stamped acquisition times, in response to correction of the first estimated location by (e.g., linearly) interpolating vessel location reference adjustments between the corrected first estimated location and a second location point in the vessel structure. The process of FIG. 6 ends at step 631.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 2-6 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system enables a user to correct mis-registration between an angiography and an IVUS image, for example, in a composite single image by selecting and adjusting location of a point on the angiography (or IVUS) image so that the adjusted point is correctly registered (as indicated by time stamps) with a marker identifying a location in the other image. Further, the processes and applications may, in alternative embodiments, be located on one or more (e.g., distributed) processing devices on a network linking the units of FIG. 2. Any of the functions and steps provided in FIGS. 2-6 may be implemented in hardware, software or a combination of both.

What is claimed is:

1. A method operable on one or more processors for providing a single composite image including a plurality of medical images of a portion of patient anatomy acquired using a corresponding plurality of different types of imaging device, comprising:
    displaying a single composite image including,
        a first image area showing a first image of an internal portion of patient anatomy acquired using a first type of imaging device and
        a second image area showing a second image of said internal portion of patient anatomy acquired using a second type of imaging device different than said first device type, said second image comprising a plurality of rows acquired at corresponding plurality of successive acquisition times and at different anatomical locations, said first and second image areas including first and second markers respectively, said first and second markers identifying an estimated location of the same corresponding anatomical position in said portion of patient anatomy in said first and second images respectively; and
    moving at least one of,
        (a) the first marker in the first image and
        (b) the second marker in the second image, to correct said estimated location so said first and second markers identify the same corresponding anatomical position in said portion of patient anatomy and said second marker identifies a row in said second image having a known acquisition time.

2. A method according to claim 1, wherein
    said first type of imaging device is an X-ray imaging device,
    said second type of imaging device is an intravascular ultrasound imaging device,
    said portion of patient anatomy comprises a vessel structure.

3. A method according to claim 2,
    further comprising respectively acquiring, by said X-ray imaging device and said ultrasound imaging device concurrently, first and second sequential series of images at time stamped acquisition times and said estimated location is derived using the timestamps of said first and second sequential series of images.

4. A method according to claim 1, wherein
    the first type of imaging device is at least one of (a) an X-ray imaging device, (b) an MR imaging device, (c) a CT scan imaging device and (d) a nuclear imaging PET scanner device.

5. A method operable on one or more processors for providing a single composite image including a plurality of medical images of a portion of patient anatomy acquired using a corresponding plurality of different types of imaging device, comprising:

storing in at least one repository a first and second sequential series of images concurrently acquired at time stamped acquisition times using an X-ray imaging device and an intravascular ultrasound imaging device respectively;

displaying a single composite image including, a first image area showing a first image of a patient internal vessel structure acquired using a first type of imaging device and         a second image area showing a second image of said patient internal vessel structure acquired using a second device type of imaging device different than said first type, said second image comprising a plurality of rows acquired at corresponding plurality of successive acquisition times and at different anatomical locations, said first and second image areas including first and second markers respectively, said first and second markers identifying a first estimated location of the same corresponding anatomical position in said patient vessel structure in said first and second images respectively;

moving at least one of,

(a) the first marker in the first image and         (b) the second marker in the second image, to correct said first estimated location so said first and second markers identify the same corresponding anatomical position in said patient vessel structure and said second marker identifies a row in said first second image having a known acquisition time; and     adjusting a timestamp of said time stamped acquisition times in response to correction of said first estimated location.

6. A method according to claim 5, wherein said first type of imaging device is an X-ray imaging device, said second type of imaging device is an intravascular ultrasound imaging device and said first estimated location is derived using the timestamps of said first and second sequential series of images.

7. A method according to claim 5, wherein the first and second markers represent one of, (a) a proximal point and (b) a distal point of said vessel structure.

8. A method according to claim 5, wherein said first and second image areas include third and fourth markers respectively, said third and fourth markers identifying a second estimated location of the same corresponding anatomical position in said patient vessel structure in said first and second images respectively and the method further comprises moving at least one of,     (a) the third marker in the first image and     (b) the fourth marker in the second image, to correct said second estimated location so said third and fourth markers identify the same corresponding anatomical position in said patient vessel structure.

9. A method according to claim 8, wherein the first and second markers represent a proximal point of said vessel structure and the third and fourth markers represent a distal point of said vessel structure.

10. A method according to claim 8, further comprising adjusting timestamps of said time stamped acquisition times in response to correction of said first estimated location by interpolating timestamp adjustments between the corrected first estimated location and a second point in said vessel structure.

11. A method according to claim 10, further comprising linearly interpolating said timestamp adjustments.

12. A method according to claim 5, further comprising adjusting timestamps of said time stamped acquisition times in response to correction of said first estimated location by interpolating timestamp adjustments between the corrected first estimated location and a second location point in said vessel structure.

13. A method according to claim 12, further comprising linearly interpolating said timestamp adjustments.

\* \* \* \* \*